United States Patent
Li et al.

(10) Patent No.: US 12,318,247 B1
(45) Date of Patent: Jun. 3, 2025

(54) EARLY DENTAL CARIES DETECTION SYSTEM AND METHOD

(71) Applicant: MLOptic Corp, Redmond, WA (US)

(72) Inventors: Junyan Li, Nanjing (CN); Wei Zhou, Sammamish, WA (US); Zhongtao Fan, Nanjing (CN)

(73) Assignee: MLOptic Corp., Redmond, WA (US)

( * ) Notice: Subject to any disclaimer, the term of this patent is extended or adjusted under 35 U.S.C. 154(b) by 0 days.

(21) Appl. No.: 18/824,859

(22) Filed: Sep. 4, 2024

(51) Int. Cl.
*A61B 8/08* (2006.01)
*A61B 8/00* (2006.01)
*A61B 8/12* (2006.01)

(52) U.S. Cl.
CPC .............. *A61B 8/0858* (2013.01); *A61B 8/12* (2013.01); *A61B 8/4494* (2013.01)

(58) Field of Classification Search
CPC ....... A61B 8/0858; A61B 8/12; A61B 8/4494; A61B 8/0875; A61B 5/0534; A61B 5/45; A61B 5/4547; A61B 5/682
See application file for complete search history.

(56) References Cited

U.S. PATENT DOCUMENTS

| | | | | |
|---|---|---|---|---|
| 4,324,546 A * | 4/1982 | Heitlinger | ........... | A61C 13/0004 433/213 |
| 4,468,197 A * | 8/1984 | Provost | ................. | A61B 5/0088 433/30 |
| 4,554,836 A * | 11/1985 | Rudd | ....................... | G01H 9/00 73/657 |
| 4,867,682 A * | 9/1989 | Hammesfahr | ........ | A61C 9/0006 433/229 |
| 5,570,182 A * | 10/1996 | Nathel | .................. | A61B 5/0066 356/477 |
| 5,818,587 A * | 10/1998 | Devaraj | ............... | A61B 5/0088 356/477 |
| 6,201,880 B1 * | 3/2001 | Elbaum | ..................... | A61B 1/24 348/66 |
| 6,413,220 B1 * | 7/2002 | Rose | ..................... | A61C 19/043 600/589 |
| 6,741,410 B2 * | 5/2004 | Plank | ..................... | G02B 6/262 606/17 |
| 7,286,954 B2 * | 10/2007 | Kopelman | .............. | G16Z 99/00 700/118 |
| 8,115,919 B2 * | 2/2012 | Yun | ........................ | G01J 3/4412 356/301 |

(Continued)

*Primary Examiner* — Cris L. Rodriguez
*Assistant Examiner* — Hao D Mai
(74) *Attorney, Agent, or Firm* — Jong Patent Firm; Cheng Ning Jong; Tracy P. Jong

(57) ABSTRACT

A system for determining dental caries in a patient's tooth, the system including a dental tray including a curved channel configured to be placed on the patient's teeth on the patient's lower jaw or below the patient's teeth on the patient's upper jaw, the channel includes a length, two side walls and a middle wall connecting the two side walls, and a U-shaped excitation-detection transducer defined by two side portions and a middle portion connecting the two side portions, the transducer configured to be supported on and slidingly coupled with the channel with a shape of the transducer conforming to a cross-sectional periphery of the channel, the transducer selectively positioned over a portion of the channel over the patient's tooth, wherein the transducer is used to excite surface acoustic waves (SAWs) in the tooth and to receive SAWs in the patient's tooth.

14 Claims, 12 Drawing Sheets

(56) References Cited

U.S. PATENT DOCUMENTS

| | | | | |
|---|---|---|---|---|
| 9,687,330 | B2* | 6/2017 | Rauscher | G01B 11/2531 |
| 10,123,706 | B2* | 11/2018 | Elbaz | H04N 13/246 |
| 10,504,386 | B2* | 12/2019 | Levin | G06T 1/0007 |
| 10,507,087 | B2* | 12/2019 | Elbaz | A61B 1/00193 |
| 10,603,008 | B2* | 3/2020 | Maev | A61C 19/04 |
| 10,849,723 | B1* | 12/2020 | Yancey | A61C 7/002 |
| 2010/0170052 | A1* | 7/2010 | Ortins | A63F 13/213 |
| | | | | 15/106 |
| 2010/0279248 | A1* | 11/2010 | Mourad | A61B 5/7275 |
| | | | | 433/29 |
| 2012/0040312 | A1* | 2/2012 | Hinders | G06T 7/0012 |
| | | | | 433/215 |
| 2015/0010878 | A1* | 1/2015 | Seibel | A61B 5/0071 |
| | | | | 433/215 |
| 2015/0217141 | A1* | 8/2015 | Barthe | A61N 7/00 |
| | | | | 601/2 |
| 2015/0313572 | A1* | 11/2015 | Gerbaulet | A61C 19/04 |
| | | | | 433/29 |
| 2017/0234837 | A1* | 8/2017 | Hall | B06B 3/00 |
| | | | | 73/602 |
| 2018/0172849 | A1* | 6/2018 | Nelson | G01T 1/20182 |
| 2019/0117078 | A1* | 4/2019 | Sharma | A61B 1/24 |
| 2019/0125297 | A1* | 5/2019 | Chan | A61B 6/481 |
| 2019/0142555 | A1* | 5/2019 | Macoskey | A61B 8/4281 |
| | | | | 433/215 |
| 2021/0302314 | A1* | 9/2021 | Kawada | A61B 1/00 |
| 2023/0200660 | A1* | 6/2023 | Sayama | G01N 21/65 |
| | | | | 433/29 |
| 2023/0225842 | A1* | 7/2023 | Glebova | A61B 5/0088 |
| | | | | 433/29 |
| 2024/0041426 | A1* | 2/2024 | Lechner | A61B 8/0875 |
| 2024/0315565 | A1* | 9/2024 | Sayama | A61B 5/7445 |

\* cited by examiner

EARLY DENTAL CARIES DETECTION SYSTEM AND METHOD

BACKGROUND OF THE INVENTION

1. The Field of the Invention

The present invention relates to the field of detection device technology. More specifically, the present invention is directed to a non-contact detection device and method for detecting early dental caries.

2. Background Art

Dental caries, a common dental hard tissue disease, is characterized by bacterial erosion of the teeth, leading to the formation of small cavities or lesions on the teeth. Normal enamel and dentin continuously deteriorate until they lose protection of the dental pulp, which is the main cause of pulpitis and periapical inflammation. The progression of dental caries is usually irreversible, but if diagnosed early, it can be restored to health through methods such as remineralization. The deeper the caries develop, the easier the diagnosis becomes, but the more difficult the treatment and recovery. Therefore, research on diagnostic techniques for early dental caries has been increasingly valued by researchers.

Traditional diagnostic methods for caries mainly include subjective diagnosis and X-ray diagnosis. However, due to the subtle clinical symptoms of early caries and the demineralized part of the teeth being distributed only in the surface layer of enamel, traditional methods cannot diagnose caries in the early stages. With the rapid development of electronic and optical imaging technologies, new developments have been made in the diagnostic techniques for early caries. These technologies mainly include light scattering, optical fiber transmission, fluorescence and dye penetration, etc. Although these methods have greatly promoted the research on the diagnosis of early caries, they still have many drawbacks, such as limited detection sites, low accuracy, susceptibility to influences such as dental calculus leading to misdiagnosis, and inability to quantitatively assess the degree of demineralization of early caries.

A conventional approach would be to utilize a contact-type ultrasound probe to achieve a similar detection process. However, the use of such a probe requires higher standards for its size and shape, as well as the use of coupling media to ensure effective transmission of ultrasound vibration into the teeth. Additionally, employing a handheld ultrasound probe may introduce instability in the results due to variations in pressure applied to the teeth during the detection process.

Laser ultrasonic technology, as an emerging non-destructive testing technology, has advantages such as non-contact, broadband excitation, and high spatial resolution. Laser-generated acoustic surface wave technology is particularly suitable for non-destructive evaluation of the near-surface elastic properties of materials. The demineralization of enamel due to dental caries leads to the loss of mineral ions such as $Ca^{2+}$ and $Mg^{2+}$, forming a porous structure, which changes its elastic properties, mainly manifested as a decrease in elastic modulus and density.

There exists a need for a system and a method for diagnosing early dental caries that is non-destructive and non-contact, e.g., one in which the change in the elastic properties of enamel is evaluated, e.g., by measuring the change in the phase velocity of laser-excited acoustic surface waves.

SUMMARY OF THE INVENTION

In accordance with the present invention, there is provided a system for determining dental caries in a patient's tooth, the system including:
 (a) a dental tray including a curved channel configured to be placed on the patient's teeth encompassing the patient's tooth on the patient's lower jaw or below the patient's teeth encompassing the patient's tooth on the patient's upper jaw, the curved channel includes a length, two side walls and a middle wall connecting the two side walls; and
 (b) a U-shaped excitation-detection transducer defined by two side portions and a middle portion connecting the two side portions, the U-shaped excitation-detection transducer configured to be supported on and slidingly coupled with the curved channel with a shape of the U-shaped excitation-detection transducer conforming to a cross-sectional periphery of the curved channel, the U-shaped excitation-detection transducer selectively positioned over a portion of the curved channel over the patient's tooth at a position along the length of the dental tray, the U-shaped excitation-detection transducer includes a pair of excitation-detection modules each disposed in a side portion of the two side portions, each excitation-detection module including an excitation device and a detection device, the excitation device including a laser configured to excite surface acoustic waves (SAWs) in the patient's tooth and the detection device configured to receive SAWs in the patient's tooth, in response to the excitation of the SAWs of the excitation device,
wherein a presence of a carious area of the patient's tooth is determined based on a departure of a phase velocity of the SAWs of the patient's tooth from a theoretical phase velocity of the SAWs of the patient's tooth.

In one embodiment, the system further includes a third excitation-detection module disposed in the middle portion of the U-shaped excitation-detection transducer. In one embodiment, the excitation device includes a laser configured to excite SAWs in the patient's tooth, with a wavelength of about 266 nm, a pulse width of about 7 ns, a single pulse energy of about 1 mJ, and a repetition frequency of about 10 Hz. In one embodiment, the dental tray is transparent to allow a detection laser beam emitted from the detection device to pass through the dental tray and reach a surface of the patient's tooth and a reflection of the detection laser beam in which SAW vibration information is embedded, to pass back through the dental tray to the detection device. In one embodiment, the dental tray further includes a platform connecting a top edge of a side wall of the two side walls interior to the curved channel, the dental tray is configured to be coupled to the patient's teeth on the patient's upper jaw, by securing the dental tray at the platform to the patient's palate. In one embodiment, the platform is constructed from silicone. In one embodiment, the system further includes a three-dimensional (3D) profilometer configured to measure an external contour of the patient's tooth to produce external contour measurements of the patient's tooth. In one embodiment, the system further includes a camera disposed within the U-shaped excitation-detection transducer and directed at a portion of the patient's tooth.

In accordance with the present invention, there is further provided a method for determining a presence and relative severity of dental caries in a patient's tooth, the method including:
(a) placing a dental tray on the patient's teeth encompassing the patient's tooth on one of the patient's lower jaw and below the patient's teeth on the patient's upper jaw, the dental tray including a curved channel including two side walls and a middle wall;
(b) positioning an excitation-detection transducer over the patient's tooth at a position along the length of the curved channel;
(c) exciting surface acoustic waves (SAWs), in the patient's tooth, using an excitation device of the excitation-detection transducer through at least the two side walls of the curved channel;
(d) receiving SAWs in response to the excitation of the SAWs of the excitation device, in the patient's tooth, using a detector device of the excitation-detection transducer; and
(e) determining the presence and relative severity of a carious area of the patient's tooth based on a departure of a phase velocity of the SAWs of the patient's tooth from a theoretical phase velocity of the SAWs of the patient's tooth.

In one embodiment, the method further includes exciting SAWs, in the patient's tooth, using the excitation device of the excitation-detection transducer through the middle wall. In one embodiment, the excitation device includes a laser configured to excite SAWs in the patient's tooth, with a wavelength of about 266 nm, a pulse width of about 7 ns, a single pulse energy of about 1 mJ, and a repetition frequency of about 10 Hz. In one embodiment, the dental tray is transparent to allow a detection laser beam emitted from the detection device to pass through the dental tray and reach a surface of the patient's tooth and a reflection of the detection laser beam in which SAW vibration information is embedded, to pass back through the dental tray to the detection device. In one embodiment, the dental tray further includes a platform connecting a top edge of a side wall of the two side walls interior to the curved channel, the dental tray is configured to be coupled to the patient's teeth on the patient's upper jaw, by securing the dental tray at the platform to the patient's palate. In one embodiment, the platform is constructed from silicone.

An object of the present invention is to provide a system and method for detecting early dental caries.

Another object of the present invention is to provide a system and method for detecting early dental caries by allowing non-contact measurements of enamel material parameters.

Another object of the present invention is to provide a system and method for quantitatively detecting early dental caries.

Whereas there may be many embodiments of the present invention, each embodiment may meet one or more of the foregoing recited objects in any combination. It is not intended that each embodiment will necessarily meet each objective. Thus, having broadly outlined the more important features of the present invention in order that the detailed description thereof may be better understood, and that the present contribution to the art may be better appreciated, there are, of course, additional features of the present invention that will be described herein and will form a part of the subject matter of this specification.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

PARTS LIST

Figure 1:
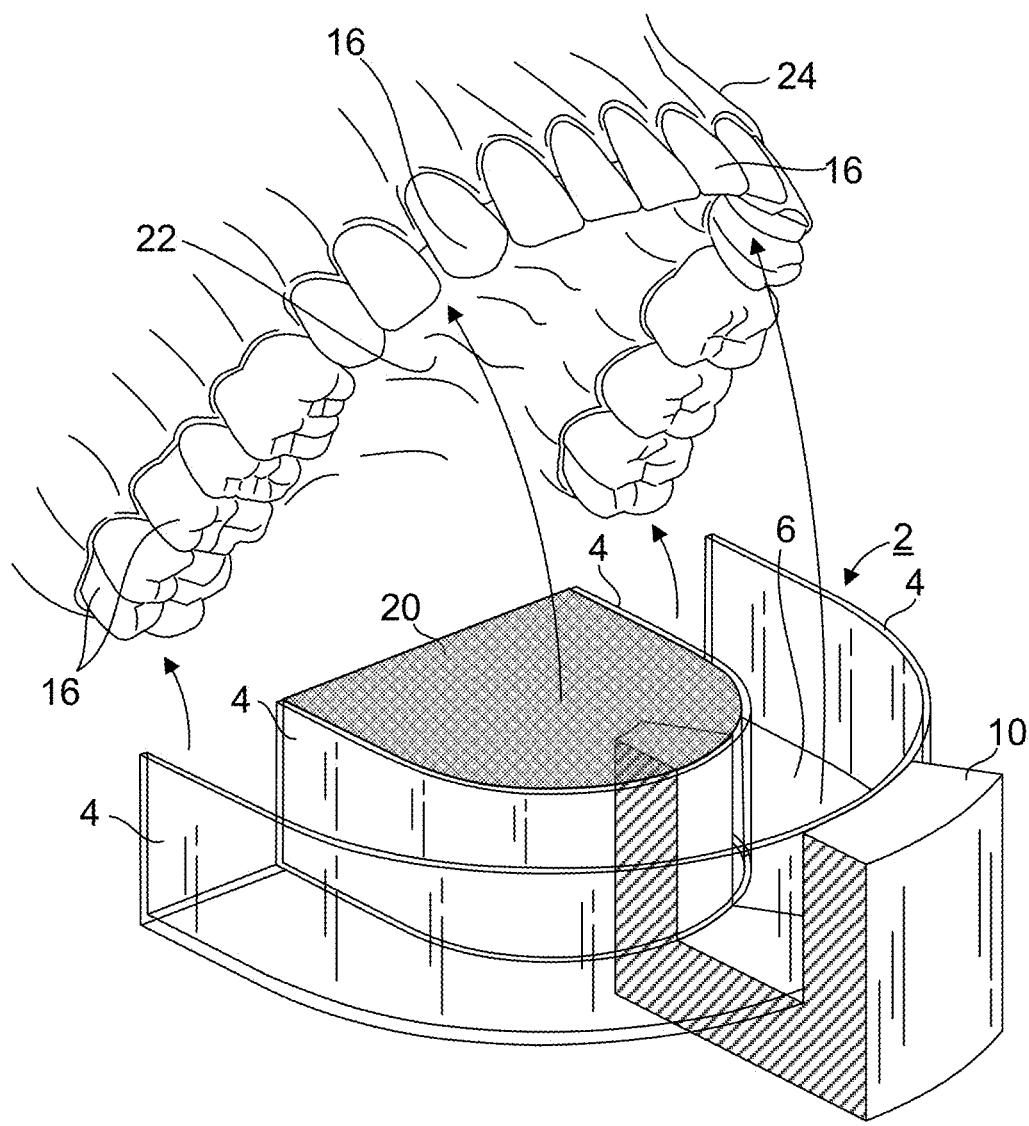
FIG. 1 is a top perspective view of a curved dental tray useful to be coupled to a patient's teeth of the upper jaw and an excitation-detection transducer shown supported on and coupled to the dental tray at a position along the length of the curved dental tray.

2—dental tray, e.g., transparent dental tray
4—side wall of dental tray
6—middle wall of dental tray
8—coordinate system of tooth under test
10—excitation-detection transducer, e.g., U-shaped excitation-detection transducer
12—lingual surface of tooth
14—tooth under test
16—teeth on upper jaw
18—teeth on lower jaw 20—platform of dental tray
22—palate
24—gum
26—excitation-detection module
28—excitation device
30—detection device
32—camera
34—controller, processor or computer
36—oscilloscope
38—translation stage driver
40—micro-mirror system driver
42—optoelectronic detection and demodulation device, e.g., phase-sensitive detector or phase-locked loop
44—buccal surface of tooth
46—solid laser
48—1×3 fiber optic splitter
50—excitation light collimator
52—mirror and f-θ lens motion device
54—two-dimensional (2D) vibration mirror
56—cylindrical lens
58—semiconductor laser generator
60—1×4 fiber optic splitter
62—acousto-optic modulator
64—fiber optic circulator
66—fiber optic coupler
68—detection laser probe including a lens
70—electrical translation stage
72—right-angle prism
74—sample 1 phase velocity vs. frequency curve
76—sample 2 phase velocity vs. frequency curve
78—sample 3 phase velocity vs. frequency curve
80—step of placing a dental tray on teeth of patient on one of patient's lower jaw and below patient's teeth on patient's upper jaw
82—step of positioning excitation device over tooth while supported on curved channel
84—step of exciting surface acoustic waves (SAWs) in patient's tooth using excitation device
86—step of receiving SAWs in response to excitation of SAWs of excitation module, in tooth, using a detector device supported on curved channel
88—step of determining a presence and relative severity of a carious area of a tooth based on a phase velocity of SAWs in tooth
90—side portion of excitation-detection transducer
92—middle portion of excitation-detection transducer
94—inner surface of excitation-detection transducer
96—occlusal surface Particular Advantages of the Invention In detecting dental caries, a transparent dental tray is used. As the transparent dental tray is placed on all the teeth on an upper jaw or all the teeth on a lower jaw, the dental tray is sufficiently secured such that an excitation-detection transducer can be securely coupled with the dental tray during use of the excitation-detection transducer and the need for a tight fixation of the dental tray to the teeth or the use of coupling media to secure the transparent dental tray to the teeth is eliminated. Without the need for a coupling medium, clearer and more accurate ultrasound signals can be detected.

As the excitation-detection transducer is configured to be placeable at any position along a channel of the dental tray, only one excitation-detection transducer is necessary as the transducer can be placed on the dental tray over a tooth to be examined. Further, as there are multiple, e.g., three, excitation-detection modules in a transducer, surface acoustic waves (SAWs) from the tooth can be obtained simultaneously from relevant excitation-detection modules, making data acquisition faster and therefore the diagnosis of dental caries faster as well and less costly. The non-contact, all-optical scanning excitation-detection transducer achieves wideband detection and rapid scanning.

DETAILED DESCRIPTION OF A PREFERRED EMBODIMENT

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

As used herein, the term "transparent dental tray," means a dental tray which is sufficiently transparent such that wavelengths of excitation light and detection light are not significantly altered by the dental tray and the optical effects of the dental tray on such wavelengths are negligible.

Figure 2:
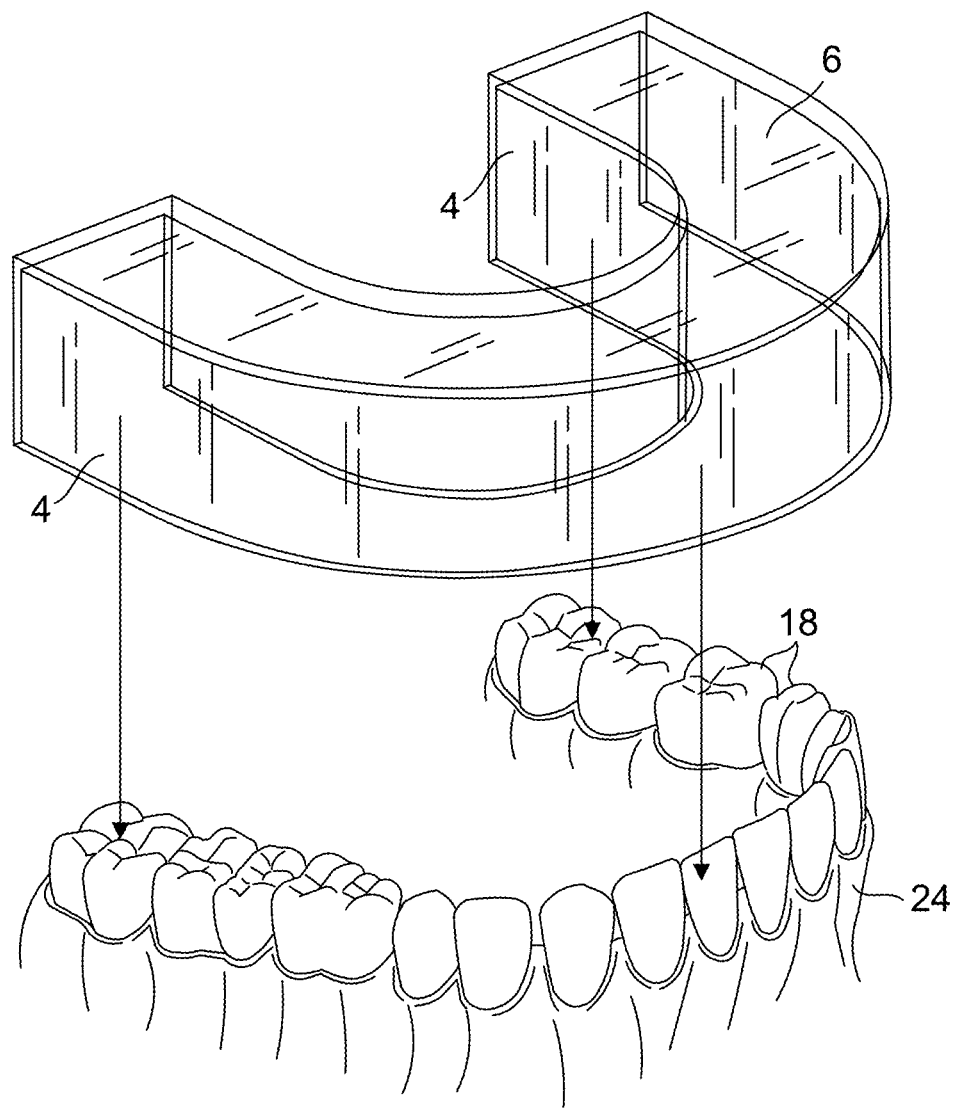
FIG. 2 is a top perspective view of a curved dental tray useful to be coupled to a patient's teeth of the lower jaw.

Disclosed herein is a system and method to address the need for early dental caries detections based on laser-excited ultrasound and interferometry to measure surface vibrations of teeth. The detection of dental caries fundamentally involves deducing material parameters of the teeth to be examined from the dispersion curves of surface acoustic waves (SAWs) within the teeth. The system and method allow for non-contact measurements of enamel material parameters, thereby allowing early dental caries to be detected and the relative extent or severity of caries development to be quantitatively assessed. FIG. 1 is a top perspective view of a curved dental tray 2 useful to be coupled to a patient's teeth 16 of the upper jaw and an excitation-detection transducer shown supported on and coupled to the dental tray at a position along the length of the curved dental tray 2. FIG. 2 is a top perspective view of a curved dental tray 2 useful to be coupled to a patient's teeth 18 of the lower jaw and an excitation-detection transducer configured to be supported on and coupled to the dental tray at a position along the length of the curved dental tray 2. The system is useful for determining dental caries in a patient's tooth of a patient and it includes a dental tray 2 and a U-shaped excitation-detection transducer 10.

The dental tray 2 includes a curved channel configured to be placed on the patient's teeth on the patient's lower jaw or below the patient's teeth on the patient's upper jaw and serves as a 'track' to support a U-shaped excitation-detection transducer. The curved channel is shaped in a manner to accommodate the common arrangement of teeth in patients although dental trays of various sizes may be made available for patients of different age groups and therefore patients with different jaw sizes. Each dental tray 2 includes a length that spans to cover a molar at one side of the patient's jaw to the other side of the patient's jaw, two side walls 4 and a middle wall 6 connecting the two side walls 4, e.g., at a right angle to the two side walls 4. Referring to FIG. 1, it shall be noted that the U-shaped excitation-detection transducer 10 is disposed below the dental tray 2 and coupled with the dental tray 2. Due to gravity, the dental tray 2 may not be securely held to the upper teeth without application of a coupling medium, e.g., dental adhesives, dental putty, temporary cement, or orthodontic wax, etc. However, a coupling medium that coats a tooth to be examined, may obscure the signals necessary to identify dental caries in the tooth, prompting the Applicant to attempt the use a platform 20 that can securely hold the dental tray 10 to a patient's palate 22, without the use of a coupling medium between the channel and the upper teeth that can cause degradation of the signals of the excitation-detection transducer. The platform 20 connects a top edge of a side wall of the two side walls 4 interior to the curved channel, allowing the dental tray 2 to be coupled to the patient's teeth on the upper jaw, by securing the dental tray at the platform 20 to the patient's palate 22. In doing so, air is evacuated between the platform and the palate to secure the dental tray 2 to the upper teeth. A lower tooth dental tray is placed on the lower teeth and secured by gravity to the lower teeth. In one embodiment, the platform is constructed from silicone, a material sufficiently pliable to conform to a patient's palate. The platform is preferably configured with a curvature similar to the palate 22.

The U-shaped excitation-detection transducer 10 is defined by two side portions 90 and a middle portion 92 connecting the two side portions 90 and configured to be supported on and slidingly coupled with the curved channel with a shape of the U-shaped excitation-detection transducer conforming to a cross-sectional periphery of the curved channel as shown in FIGS. 1 and 2. The U-shaped excitation-detection transducer 2 may be positioned over any portion of the curved channel over a tooth 14 to be tested or examined along the length of the dental tray 2. The U-shaped excitation-detection transducer 10 includes a pair of excitation-detection modules 26 each disposed in a side portion of the two side portions 90. A third excitation-detection module 26 is disposed in the middle portion 92 of the U-shaped excitation-detection transducer 10 although this module 26 may not be needed depending on the type of tooth being examined. A molar is an example of a tooth where there are three surfaces, i.e., lingual, buccal, and occlusal surfaces that are all important to be examined. However, another type of tooth, e.g., incisor, has only two prominent surfaces, i.e., lingual and buccal surfaces, upon which SAWs can be examined. Therefore, having a third excitation-detection module 26 disposed in the middle portion 12 of the U-shaped excitation-detection transducer 10 ensures that the occlusal surface of a tooth, e.g., a molar, can be examined as well.

Figure 3:
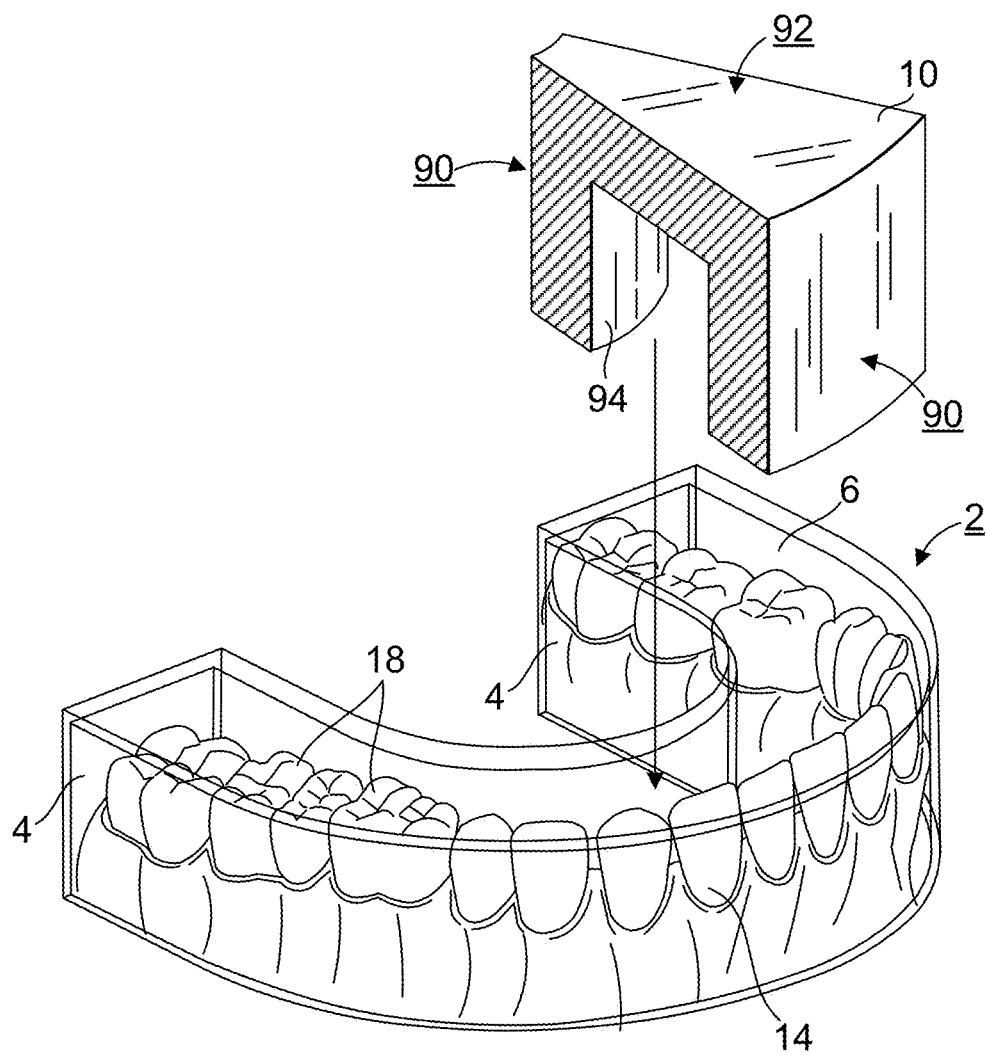
FIG. 3 is a top perspective view of a curved dental tray having been coupled to a patient's teeth of the lower jaw and an excitation-detection transducer positioned to be supported on and coupled to the dental tray at a position along the length of the curved dental tray.
Figure 4:
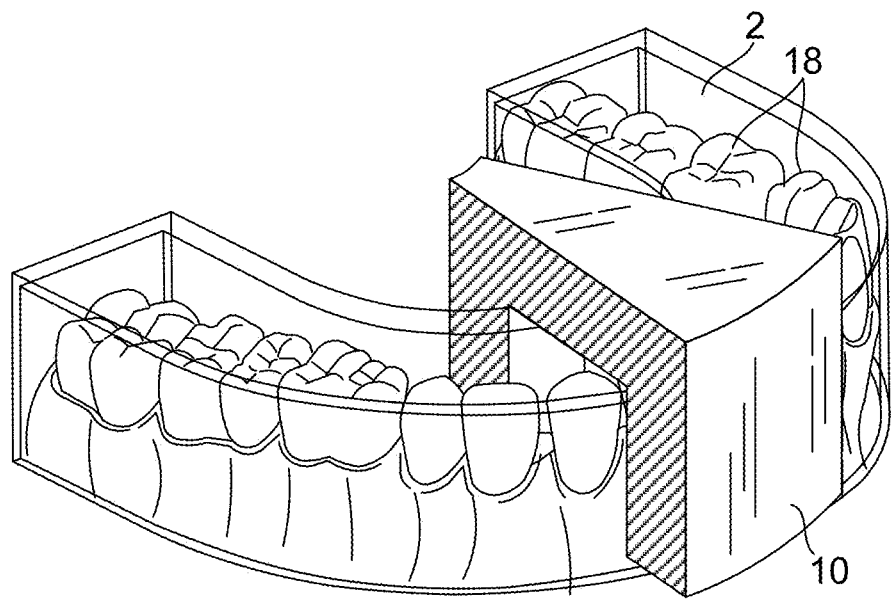
FIG. 4 is a top perspective view of a curved dental tray having been coupled to a patient's lower teeth and a U-shaped excitation-detection transducer having also been coupled with the curved dental tray.
Figure 5:
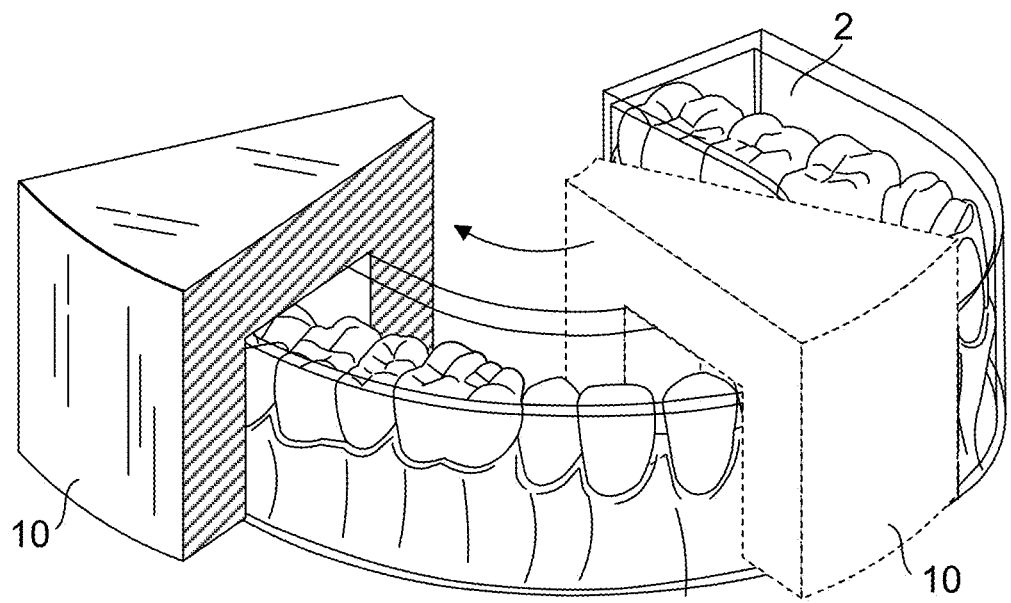
FIG. 5 is a top perspective view of a curved dental tray having been coupled to a patient's lower teeth and a U-shaped excitation-detection transducer having been coupled with the curved dental tray and positioned at a different location than the one shown in FIG. 4.

FIG. 3 is a top perspective view of a curved dental tray having been coupled to a patient's teeth of the lower jaw and an excitation-detection transducer 10 positioned to be supported on and coupled to the dental tray at a position along the length of the curved dental tray 2. FIG. 4 is a top perspective view of a curved dental tray having been coupled to a patient's lower teeth and a U-shaped excitation-detection transducer 10 having also been coupled with the curved dental tray 2. It shall be noted that the U-shaped excitation-detection transducer 10 is shaped in a manner suitable to be coupled to the curved channel of the dental tray 2. FIG. 5 is a top perspective view of a curved dental tray having been coupled to a patient's lower teeth and a U-shaped excitation-detection transducer having been coupled with the curved dental tray and positioned at a different location than the one shown in FIG. 4. It shall be noted that the inner surfaces or surfaces facing the channel, e.g., surface 94, are configured to surround the channel of the dental tray 2 and conforms to the curvature of the curved channel to allow a snug fit which also allows the U-shaped excitation-detection transducer 10 to slide along the channel for position adjustments along the length of the channel. For instance, in using the U-shaped excitation-detection transducer 10 to examine a tooth, the U-shaped excitation-detection transducer 10 may be first be disposed anywhere along the length the channel of the dental tray 2 and then subsequently moved, by sliding the transducer 10, along the channel, to a position over the tooth, preferably with the transducer 10 already within the vicinity of the tooth to avoid having to slide the transducer 10 over a long distance along the channel to a desired location for examining a tooth. Upon examining a tooth, the U-shaped excitation-detection transducer 10 may alternatively be lifted from its position while the tooth was examined to be placed at a new location along the channel such that another tooth at the new location can be examined.

Figure 6:
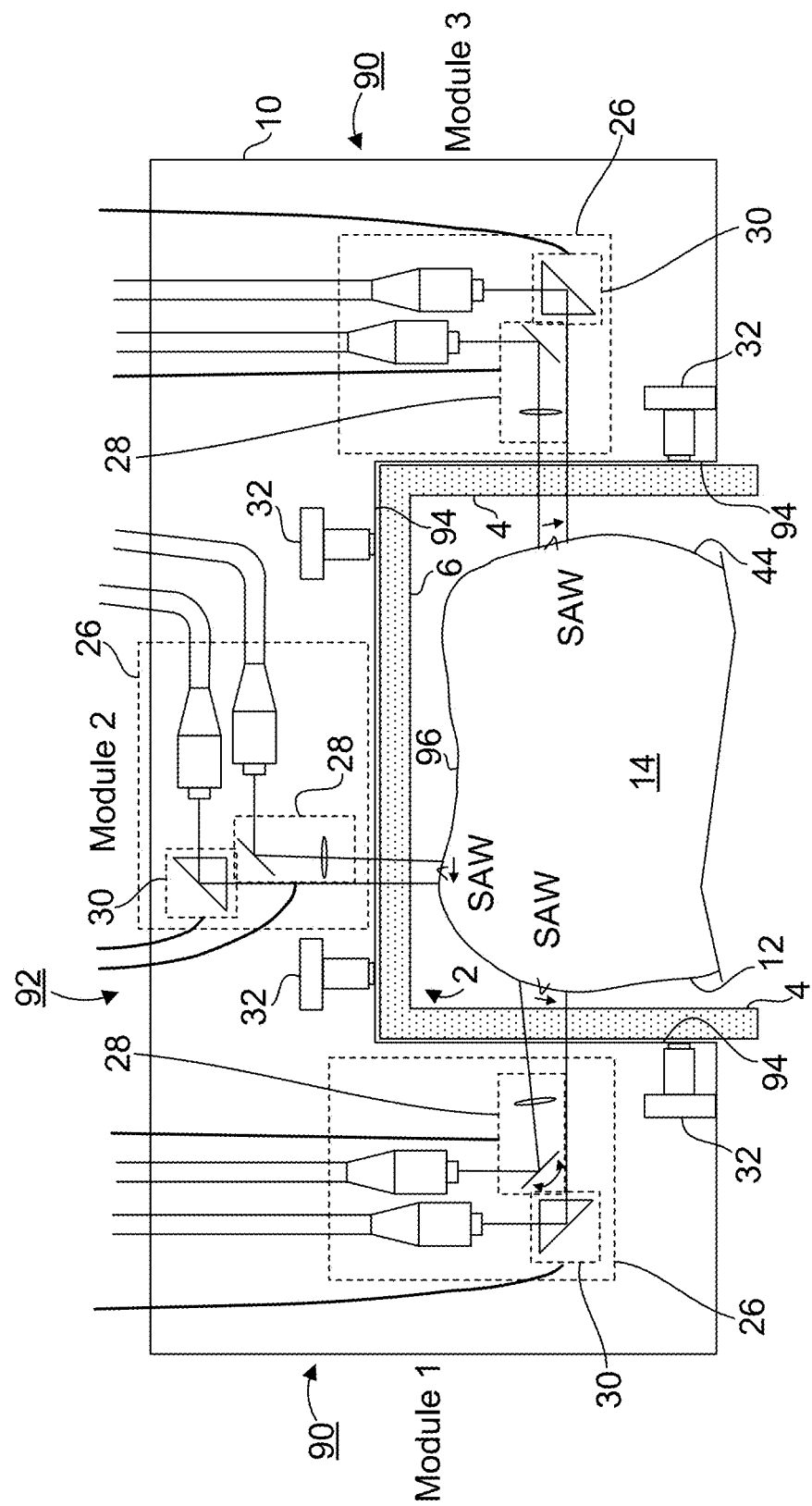
FIG. 6 is a diagram depicting a cross-sectional view of a U-shaped excitation-detection transducer having been coupled to a curved dental tray with the U-shaped excitation-detection transducer positioned over a molar.

FIG. 6 is a diagram depicting a cross-sectional view of a U-shaped excitation-detection transducer having been coupled to a curved dental tray with the U-shaped excitation-detection transducer positioned over a tooth under test 14, i.e., a molar or a premolar. An excitation-detection module 26 is disposed within each side portion 94 of the excitation-detection transducer and the middle portion of the 12 of the excitation-detection transducer with the outputs of the excitation device 28 and the detection device 30 directed through inner surfaces 94 and the channel at the tooth under test 14 on lingual and buccal surfaces 12, 44 for the excitation-detection module 26 disposed within each side portion 90 of the excitation-detection transducer and occlusal surface for the excitation-detection module 26 disposed within middle portion 92 of the excitation-detection transducer. It shall be understood that as a molar includes a broad surface, i.e., occlusal surface that is disposed substantially at a right angle with lingual and buccal surfaces, the excitation-detection modules directed for these two surfaces would not be adequately directed at the occlusal surface 96, requiring the use of a third module directed at the occlusal surface. Each excitation-detection module 26 is directed at a prominent surface, e.g., a lingual surface 12, a buccal surface 44 and an occlusal surface 96 at substantially a right angle. As each premolar has a prominent occlusal surface 96 as in the case of a molar, the excitation-detection module 26 directed at the occlusal surface 96 of a premolar is also used to examine the premolar.

Figure 7:
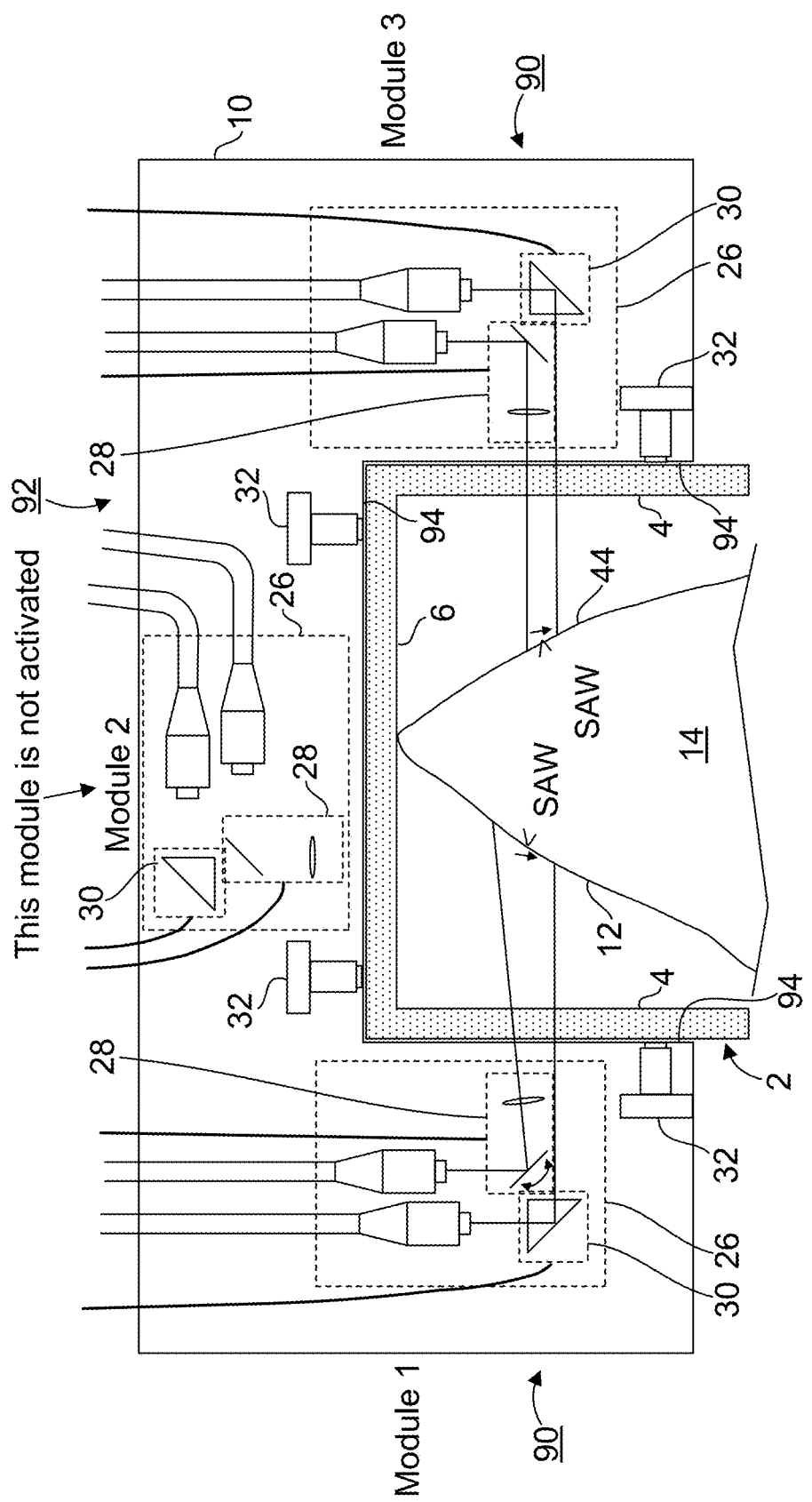
FIG. 7 is a diagram depicting a cross-sectional view of a U-shaped excitation-detection transducer having been coupled to a curved dental tray with the U-shaped excitation-detection transducer positioned over an incisor.

FIG. 7 is a diagram depicting a cross-sectional view of a U-shaped excitation-detection transducer having been coupled to a curved dental tray with the U-shaped excitation-detection transducer positioned over an incisor or a canine. It shall be noted that, for an incisor or a canine, there are only two prominent surfaces, i.e., the lingual and buccal surfaces 12, 44. Therefore, the excitation-detection module 26 disposed in the middle portion of the transducer shall not be activated to prevent signals from the excitation device of the module 26 to be inadvertently comingled with signals from the two modules facing the lingual and buccal surfaces 12, 44. As such, a U-shaped excitation-detection transducer may be configured without a module 26 in the middle portion of the transducer when an examination is carried out on a suspected tooth that is an incisor or a canine. Therefore, it can be seen that the use of only two or all three modules of the transducer depends on the morphology of the tooth to be tested, i.e., a tooth with or without a prominent occlusal surface. All three modules can be simultaneously activated such that data can be collected all at once, saving time in data collection for dental caries evaluation at a later time.

Referring back to FIGS. 6 and 7, multiple cameras 32 may be provided and disposed in the U-shaped excitation-detection transducer to capture images of a tooth being examined. The image data received from the cameras 32 can be used alongside 3D contours or the 3D tooth model obtained using a profilometer to properly identify the regions of the tooth surfaces evaluated. In the embodiment shown, a camera 32 is disposed in each side portion 94 of the U-shaped excitation-detection transducer and two cameras 32 are disposed in the middle portion 12 of the U-shaped excitation-detection transducer with the image-receiving ends of the cameras 32 pointed at the tooth being examined.

Figure 8:
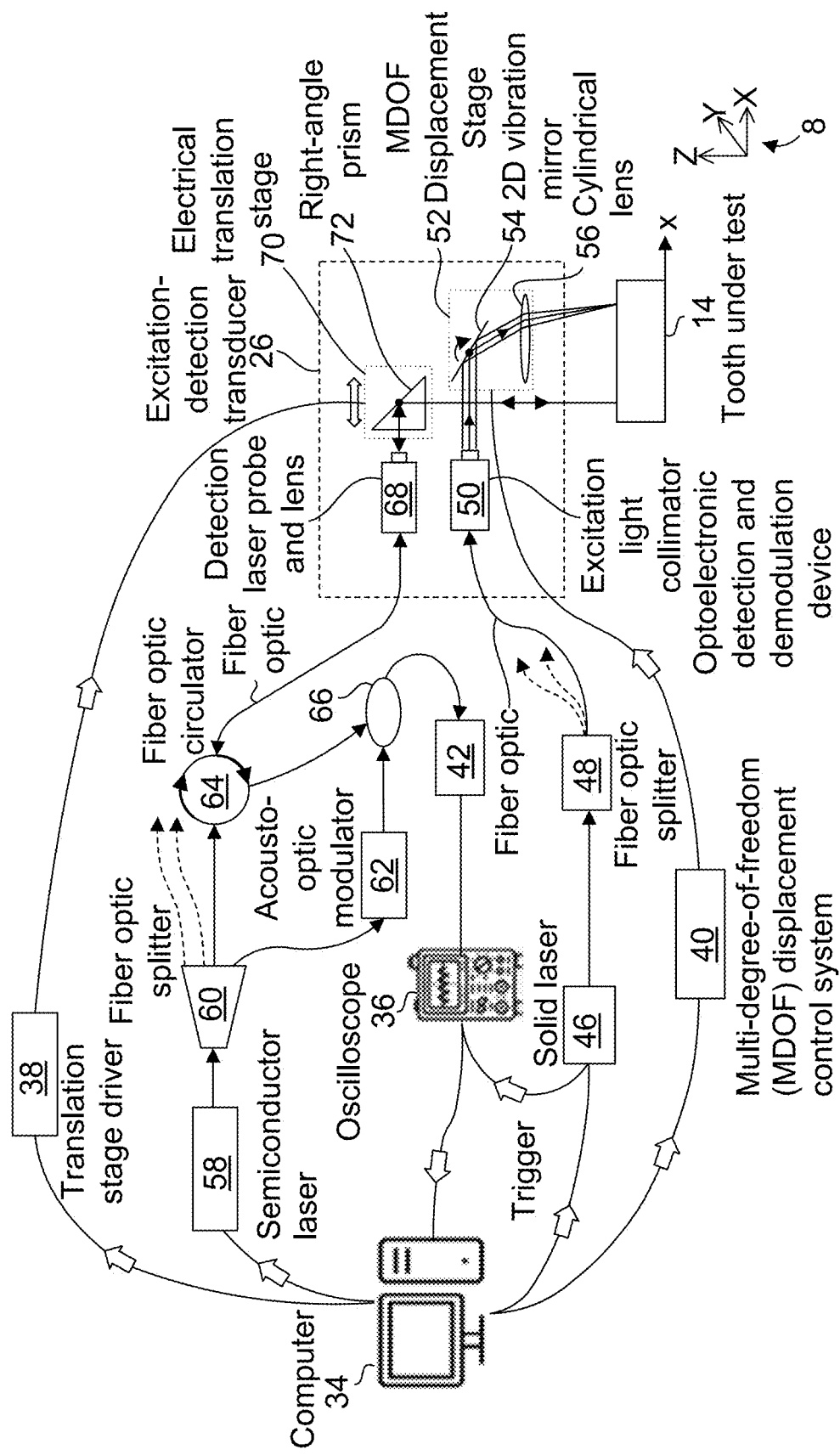
FIG. 8 is a diagram detailing a manner in which a U-shaped excitation-detection transducer functions in detecting dental caries in a tooth.

FIG. 8 is a diagram detailing a manner in which a U-shaped excitation-detection transducer functions in detecting dental caries in a tooth under test 14. A controller, processor or computer 34 is functionally connected to the U-shaped excitation-detection module that is disposed within a housing to protect an excitation device and a detection device contained therein from the intrusion of saliva and other fluids while the module is being used or cleaned. The excitation device 28 includes an excitation light collimator 50 useful for collimating a laser beam transmitted via a fiber optic through a two-dimensional (2D) vibration mirror 54 and a cylindrical lens 56 to the tooth under test 14, both of which are controlled using a multi-degree-of-freedom displacement stage 52 which is in turn controlled using a multi-degree-of-freedom displacement control system driver 40. A pulsed solid laser 46 is configured to emit an excitation light, triggering a signal to oscilloscope 36, which marks the start of the recordation of a waveform. The laser excites SAWs in a tooth under test 14, where the laser wavelength is about 266 nm, the pulse width is about 7 ns, a single pulse energy of about 1 mJ, and a repetition frequency of about 10 Hz and these SAWs propagate along the tooth surface and carry information about the surface structure and material properties of the tooth. The excitation light is split into three paths by a fiber optic splitter 48 and subsequently reflected by the 2D vibration mirror 54, before being focused by the cylindrical lens 56 into a line-shaped laser source with a width of about 0.01 mm, which is then incident on the lingual, buccal, and occlusal surfaces. The 2D vibration mirror 54 and cylindrical lens 56 are fixed on a multi-degree-of-freedom displacement stage 52, useful for precisely controlling the position of the line-shaped excitation light on the tooth surface, thereby enabling changes in the excitation position of the light source on the tooth under test 14. The stepper motor resolution is about 1 μm, i.e., the stepper motor is capable of being stepped in about 1 μm increments. The mirror has two degrees of freedom in the X and Y directions, with the surface of the tooth under test 14 approximately parallel to the XY plane. The excitation light is fixed in the Y direction, and the mirror is controlled to move the laser along the X direction at a fixed highly precise step size. With the detection light of the detection device fixed, the excitation light of the excitation device is moved in steps of Δ to obtain multiple sets of SAW time-domain signals, with a sampling frequency of F_s. In obtaining a response for exciting SAWs in the tooth under test, instead of the SAWs being directly transmitted through the transparent dental tray, another visible laser beam or detection light is emitted from a detection laser head of a detection device to detect the SAW signals based on interferometry. In detecting SAWs and in response to the excitation device having been activated, the continuous-wave semiconductor laser generator 58 disposed at an output frequency of fc, is configured to emit a detection light split into four paths by a fiber optic splitter 60. One of the four paths serves as a reference light, while the other three paths enter the detection devices in the lingual, buccal, and occlusal surfaces, respectively. An acousto-optic modulator 62 then shifts the reference light frequency. After shifting, the frequency of the reference light becomes fc+fa. The measurement light enters through port 1 of the fiber optic circulator 64 and exits through port 2, and is then guided by optical lenses into the fiber optic path. A laser beam generated by the semiconductor laser generator 58 is reflected by a right-angle prism 72 and then incident on the surface of the tooth under test 14. An electronic linear translation stage 70 controlled using a translation stage driver 38, is configured to move the right-angle prism 72 to aid in disposing the right-angle prism 72 at a suitable position to guide the laser beam to be incident at an appropriate position on the tooth surface 14 before being reflected from the tooth surface back to the detection device. The detection laser beam of the detection device essentially passes through the transparent dental tray 2 and incident upon the tooth 14 surface, where the detection laser beam is reflected and then passes back through the transparent dental tray 2 to a detection laser head of the detection device. When the SAWs, a product of the excitation device 28, propagate to the location of the tooth surface where the detection laser spot is located, the SAWs cause the tooth 14 surface at that location to vibrate, and the reflected beam of the detection device 30 from that surface also carries the SAW vibration information. The returning vibration-carrying laser beam interferes with the incident or reference beam, and the interference signal is demodulated to obtain the SAW time-domain signal. The detection laser probe 68 and the right-angle prism 72 can be controlled to rotate around the Z-axis to direct a laser beam to be incident at different Y-coordinate positions of the tooth under test 14. Note the direction of the X-axis being a direction pointing to the right, the direction of the Y-axis being a direction pointing into the figure and the Z-axis being a direction pointing upwardly. This way, the positions of the detection light in both the X and Y directions can be adjusted, to more closely correspond with the scanning trajectory of the excitation light. After the measurement light returns from the tooth under test 14, it enters the fiber optic path through optical lenses. Due to the doppler effect, a frequency shift Δf occurs. The reference light and measurement light converge and interfere in the fiber optic coupler 66, with the measurement light entering through port 2 and exiting through port 3 of the fiber optic circulator 64. The displacement signal of the ultrasound vibration is loaded into the difference frequency signal fa-Δf, and a demodulation of the output current of the photodetector yields the ultrasound vibration displacement signal. The photocurrent signal can be demodulated by a demodulation device 42, e.g., phase-sensitive detectors, phase-locked loops, or spectrum analyzers, etc. The ultrasonic time-domain signals detected at each scanning position are then recorded, with the detection light fixed during the scanning process, to obtain ultrasound B-scan images of the scanned area. A 2D Fourier transform is then performed on the ultrasound B-scan results to obtain actual dispersion curves D_i reflecting the phase velocity-frequency relationship of the detection area. The results are evaluated to quantitatively evaluate the health status of the enamel, the size of carious areas, and the depth of caries in the detected teeth. The phase velocity of the surface acoustic wave reflects the presence and size of carious areas or relative severity in the enamel. The propagation characteristics of sound waves at different frequency components can reflect the depth of caries development beneath the tooth surface. Upon collecting the necessary data for the tooth under test, the U-shaped excitation-detection transducer is ready to be positioned for analyzing the next tooth. The excitation and detection processes can then be repeated such that the necessary data for the next data is collected. If necessary, this process is repeated for the remaining teeth in the patient's mouth. It shall be noted that the dental tray 2 is transparent to allow excitation light of the excitation device to be transmitted through the dental tray 2 to the tooth and excited SAWs in the tooth to be transmitted through the dental tray to the detection device. It can be seen that each excitation-detection module includes two main parts, an excitation device and a detection device, both of which are non-contact devices which do not present a mechanical and/or a chemical risk in detecting dental caries.

Figure 9:
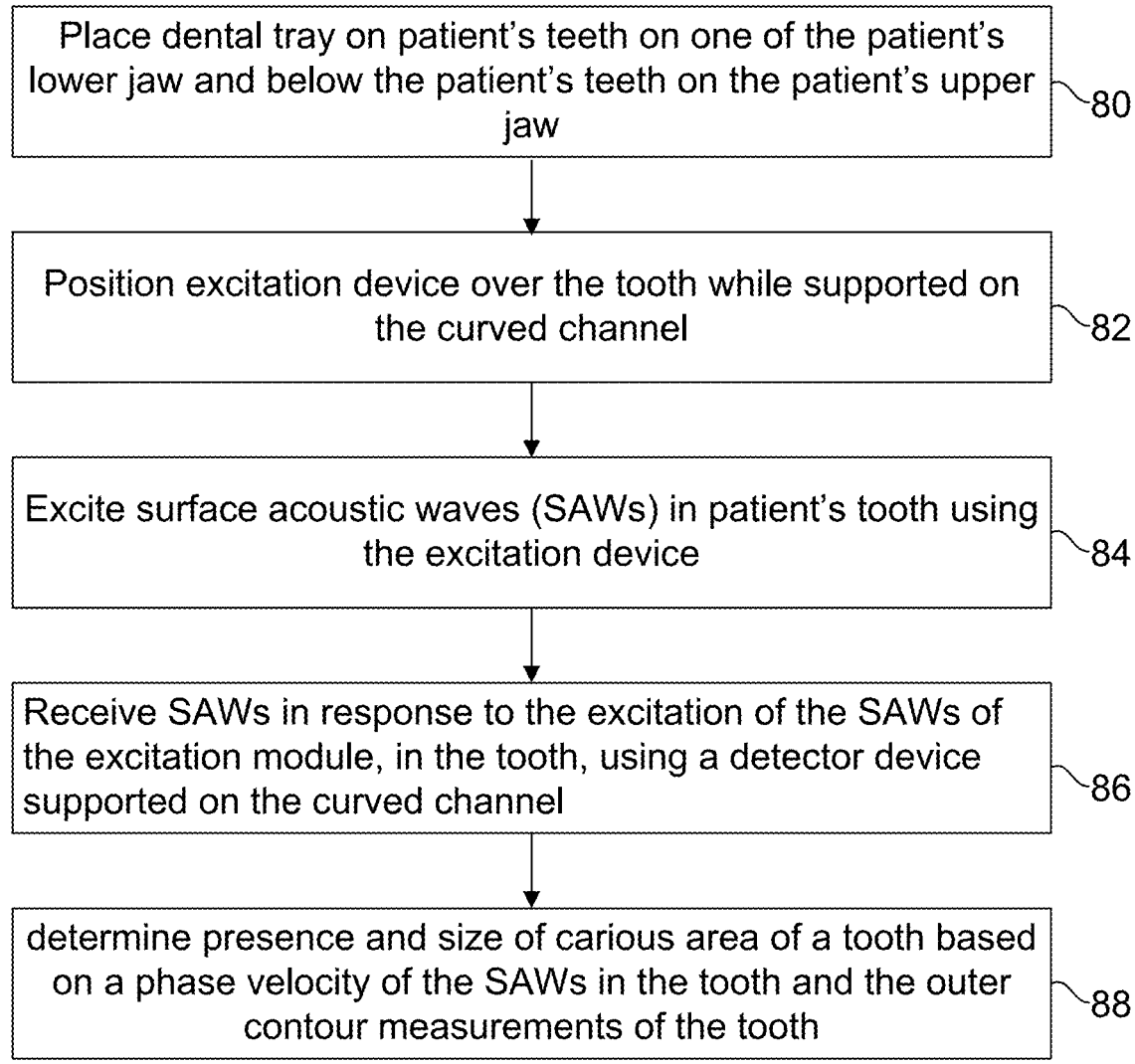
FIG. 9 is a flowchart summarizing a process for determining the presence and relative severity of dental caries in a patient's tooth.

FIG. 9 is a flowchart summarizing a process for determining the presence and relative severity of dental caries in a patient's tooth. A dental tray 2 is then placed on the teeth of the patient on the patient's lower jaw or below the patient's teeth on the patient's upper jaw depending on the location of the tooth to be examined as shown in step 80. An excitation-detection transducer is then positioned over the patient's tooth at a position along the length of the curved channel as shown in step 82. SAWs are excited in the patient's tooth using an excitation device of the excitation-detection transducer through at least the two side walls of the curved channel as shown in step 84. SAWs are received in response to the excitation of the SAWs of the excitation device, in the patient's tooth, using a detector device of the excitation-detection transducer as shown in step 86. A presence and relative severity of a carious area are determined of the patient's tooth based on a phase velocity of the SAWs in the patient's tooth as shown in step 88.

Applicant discovered that dispersion curves of surface acoustic waves are influenced not only by the material parameters of the medium examined but also by the geometric shape of the medium, including the surface contours of the teeth and the thickness of the enamel. For a tooth that is well-formed and has relatively flat (large radius of curvature or small curvature) lingual, buccal and occlusal surfaces, dispersion curves of SAWs obtained of such surfaces can be relied upon. The center wavelength of the SAWs excited by the excitation light in a tooth under test is about 0.5 mm. When the radius of curvature of a portion of a tooth surface is greater than about 20 times the center wavelength, i.e., the radius of curvature is greater than about 10 mm, the performance of the SAWs propagating in that area is no different from that propagating in a flat plate and the surface can be considered relatively flat. Otherwise, in order to accurately deduce the material parameters related to the development of dental caries from the dispersion curves of SAWs, it is first necessary to eliminate the effects of the medium's geometric shape on the propagation of SAWs. A tooth that is not considered well-formed may still have surface regions that are considered sufficiently flat and featureless such that SAWs obtained of these regions separately can be reliably used to indicate the presence and relative severity of dental caries. Therefore, multiple sets of SAWs may be obtained and analyzed with a set of SAWs corresponding to a region of a surface, i.e., lingual, buccal and occlusal surface being examined.

Figure 10:
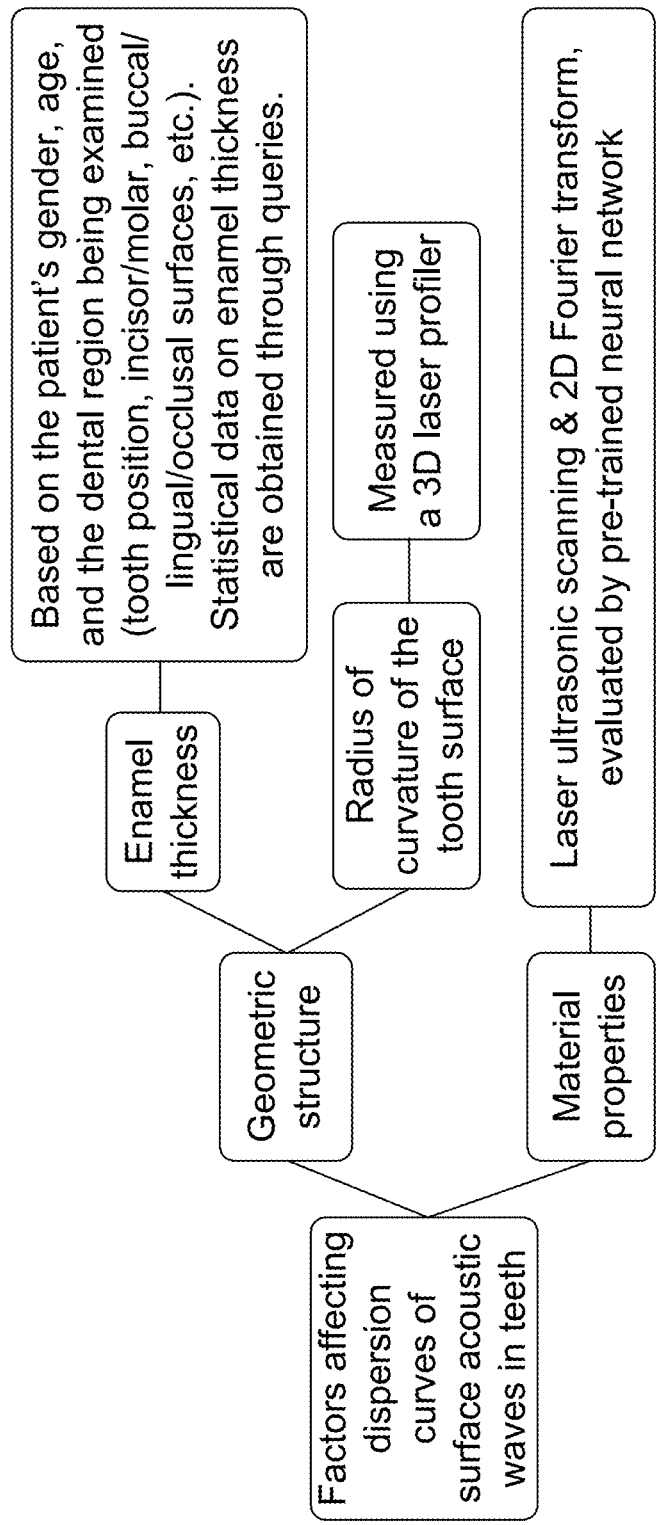
FIG. 10 is a diagram depicting factors affecting dispersion curves of surface acoustic waves (SAWs) in teeth.
Figure 11:
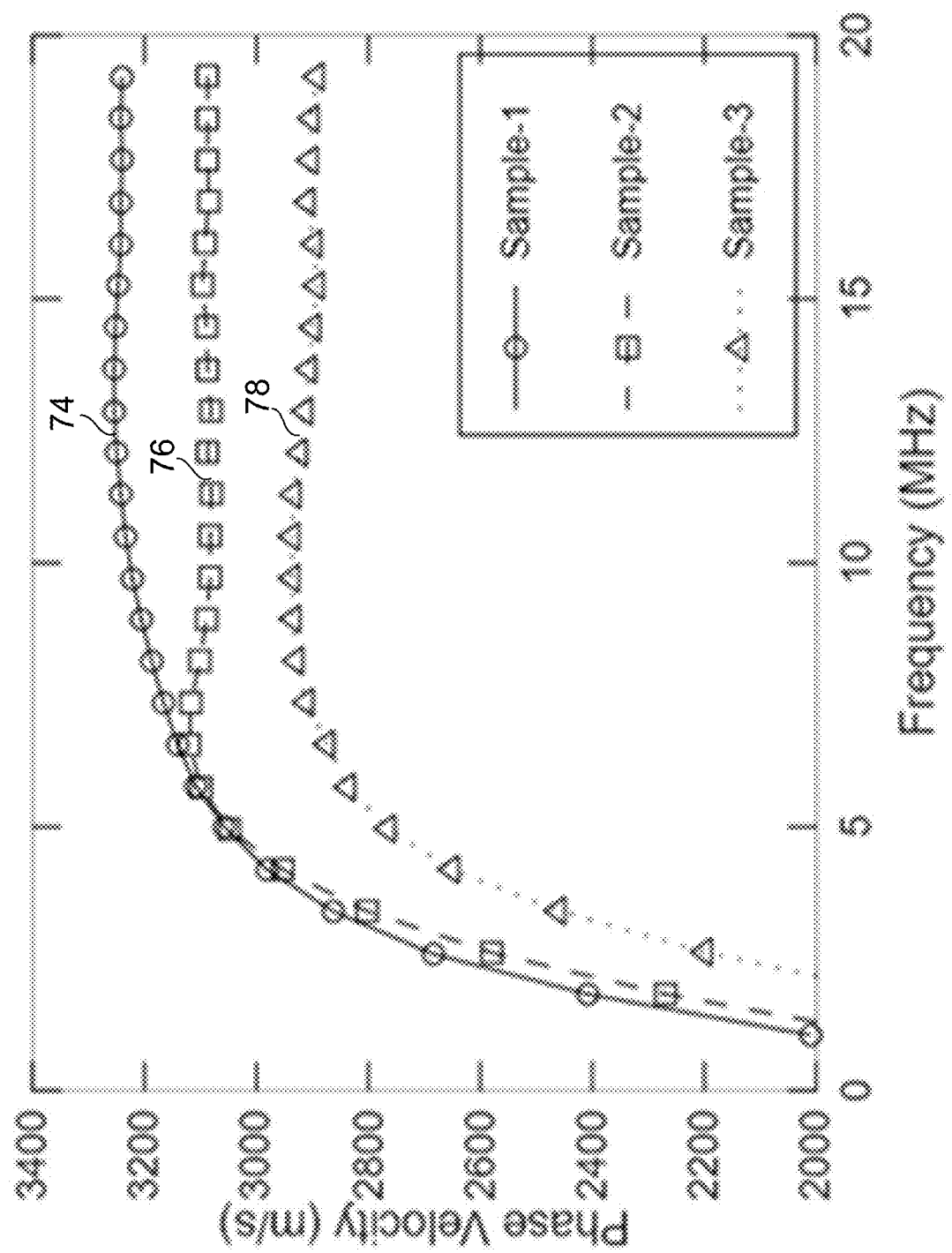
FIG. 11 shows dispersion curves of the phase velocity of SAWs in teeth with different degrees of caries.

FIG. 10 is a diagram depicting factors affecting dispersion curves of SAWs in teeth, e.g., the geometric structure and material properties of the teeth. The geometric structure of a tooth deals with the enamel thickness of the tooth and the radius of curvature of the tooth surface. The radius of curvature of a region or the entirety of a tooth surface may be measured using a 3D laser profilometer, e.g., 3Shape TRIOS® 3 Intraoral Scanner. Based on changes in the surface curvature radius of a surface of a tooth, the surface may be modelled as m regions, each region's curvature being approximated as a constant. Using the Finite Element Method (FEM) in the frequency domain, theoretical values of the dispersion curve H of SAWs propagating along a surface or different regions of a surface or theoretical values of the dispersion curves H_i of SAWs propagating along different regions of a surface, can be established, where i=1, 2, 3, . . . , m. H_i records the relationship between angular frequency ω and wave number k, which can be converted into the relationship between frequency f and phase velocity v_p using the formulas f=ω/2π and v_p=ω/k. Using the laser ultrasonic excitation-detection device disclosed elsewhere herein, the m regions can be scanned sequentially or only select region/s of interest of the regions may be scanned. With the detection light fixed, the excitation light is moved in steps of Δs to obtain multiple sets of SAW time-domain signals, with a sampling frequency of F_s. A 2D Fourier transform is performed on the results to obtain the actual dispersion curve D_i of the detection area, where i=1, 2, 3, . . . , m. By comparing D_i with H_i, a difference between them is indicative of changes in the propagation characteristics of surface acoustic waves caused by changes in enamel material parameters. In one example, H_i may be represented as Sample-1 curve 74 shown in FIG. 11 which shows the dispersion curves 74, 76, 78 of the phase velocity of SAWs in teeth with different degrees of caries. Sample-1 represents a theoretical dispersion curve obtained from a healthy tooth. Sample-2 represents a tooth with mild caries, and sample-3 represents a tooth with severe caries. It shall be noted that, at a particular frequency, the phase velocity of the SAWs of a tooth with caries tends to be below the phase velocity of SAWs of a tooth without caries. A D_i curve or D_i curves may approximate the Sample-1 curve if no early dental caries has been present in the tooth under test. It shall be noted that a departure of more than about 3-5% of a D_i curve from the H_i curve/s, i.e., phase velocity of 3-5% below the baseline phase velocity, signifies the presence of early dental caries and the degree of departure of a D_i curve from the H_i curve/s is proportional to the severity of early dental caries.

Figure 12:
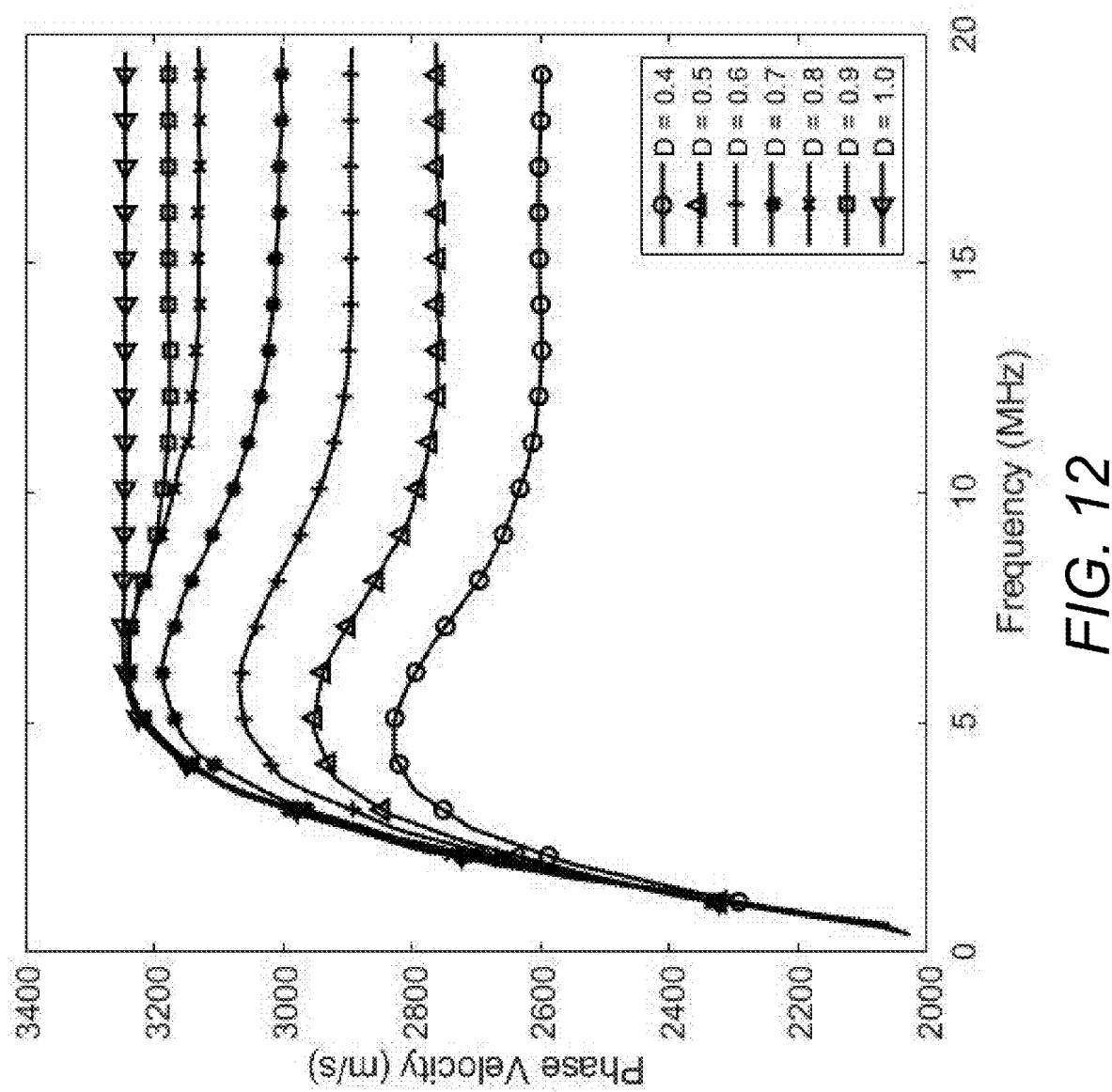
FIG. 12 shows the dispersion curve of SAWs in early caries with different demineralization coefficients Cs with a constant thickness of white spot lesion (WSL) 1 mm.
Figure 13:
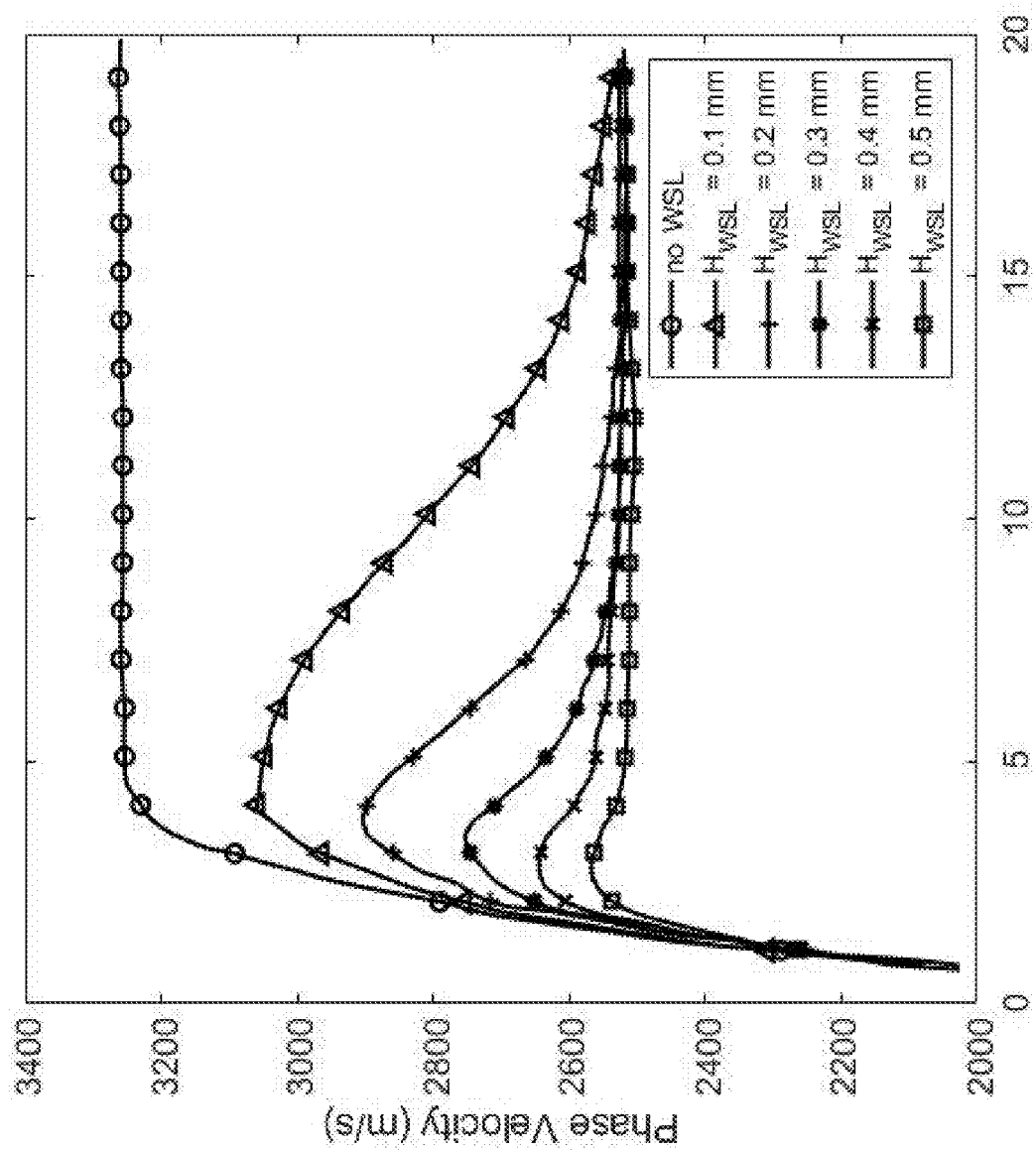
FIG. 13 shows the dispersion curves of SAWs in early caries with different thicknesses of WSL and a constant demineralization coefficient C at 0.6.

The formation of early dental caries is essentially due to the breakdown of minerals in the enamel by bacteria, resulting in white spot lesion (WSL) on the teeth. The elastic modulus E and thickness of WSL reflect the degree of early caries development. In one aspect, the essence of quantitative evaluation of the development of early dental caries is to measure two parameters of the WSL, i.e., the elastic modulus E and thickness of the WSL. A demineralization coefficient C of the enamel can be defined based on the ratio of the elastic modulus of the WSL to the elastic modulus of healthy enamel, or:

$$C = (E\_caries\hat{\ }0)/E\_enamel \quad \text{Equation 1:}$$

where E_enamel is the elastic modulus of healthy enamel, and E_caries^0 represents the elastic modulus of the surface of the WSL. The enamel thickness may be obtained through queries of statistical data based on the patient's gender, age, and the dental region being examined, e.g., the tooth position, the type of tooth, e.g., incisor or molar and the surface being examined, e.g., buccal, lingual or occlusal surface, etc. The radius of curvature of a region of a tooth or the radius of curvature of a tooth surface is combined with statistical information on human enamel and dentin thickness to create a 3D computer model of the patient's tooth. The material parameters of this model can be set to the average values of healthy tooth materials. A smaller D indicates a greater degree of demineralization. When C=1, it indicates that no WSL exists. The distribution of elastic modulus of the general enamel layer with depth z below the tooth surface is:

$$E(z) = ((1-C) \cdot E\_enamel) \cdot z/T\_WSL + C \cdot E\_enamel \quad \text{Equation 2:}$$

where T_WSL is the thickness of the WSL. In some instances, while evaluating dental caries, these two main parameters that affect the degree of demineralization are separated, keeping one constant and changing the other, and the relationship between the degree of enamel demineralization and these two parameters, is studied through extensive FEM numerical simulations. For instance, the thickness of the WSL is kept constant at 1 mm and the SAW dispersion curves for different demineralization coefficients C were calculated and plotted, as shown in FIG. 12. It shall be noted that, at a particular frequency, the phase velocity of the SAWs of a tooth with a lower C tends to be below the phase velocity of SAWs of a tooth without caries, i.e., with C=1. The phase velocity vs. frequency of the SAWs derived from the SAWs received at the detection device may be compared with the curves of this chart to place the elastic modulus E of the patient's tooth 14 with respect to the curves corresponding to various elastic moduli. In evaluating the depth of caries, a series of SAW dispersion curves of various depths are generated based on Equation 2 and plotted as shown in FIG. 13, by holding the demineralization coefficient C constant. The phase velocity vs. frequency of the SAWs derived from the SAWs received at the detection device may also be compared with the curves of this chart to place the depth of caries in the patient's tooth 14 with respect to the curves corresponding to various depths. Similarly, a series of SAW dispersion curves that characterize the degree of caries development for different C and T_WSL values, may be generated. The dispersion curves shown in FIGS. 11-13 may be used as inputs, and C and T_WSL values as outputs to train a neural network. In detecting dental caries in a patient, the present system is used for measuring SAWs and generating dispersion curves in certain areas of the patient's tooth surface as inputs to result in a presence, size and depth of a carious area from the neural network.

The detailed description refers to the accompanying drawings that show, by way of illustration, specific aspects and embodiments in which the present disclosed embodiments may be practiced. These embodiments are described in sufficient detail to enable those skilled in the art to practice aspects of the present invention. Other embodiments may be utilized, and changes may be made without departing from the scope of the disclosed embodiments. The various embodiments can be combined with one or more other embodiments to form new embodiments. The detailed description is, therefore, not to be taken in a limiting sense, and the scope of the present invention is defined only by the appended claims, with the full scope of equivalents to which they may be entitled. It will be appreciated by those of ordinary skill in the art that any arrangement that is calculated to achieve the same purpose may be substituted for the specific embodiments shown. This application is intended to cover any adaptations or variations of embodiments of the present invention. It is to be understood that the above description is intended to be illustrative, and not restrictive, and that the phraseology or terminology employed herein is for the purpose of description and not of limitation. Combinations of the above embodiments and other embodiments will be apparent to those of skill in the art upon studying the above description. The scope of the present disclosed embodiments includes any other applications in which embodiments of the above structures and fabrication methods are used. The scope of the embodiments should be determined with reference to the appended claims, along with the full scope of equivalents to which such claims are entitled.

What is claimed herein is:

1. A system for determining dental caries in a patient's tooth, said system comprising:
   (a) a dental tray comprising a curved channel configured to be placed on the patient's teeth encompassing the patient's tooth on the patient's lower jaw or below the patient's teeth encompassing the patient's tooth on the patient's upper jaw, said curved channel comprises a length, two side walls and a middle wall connecting said two side walls; and
   (b) a U-shaped excitation-detection transducer defined by two side portions and a middle portion connecting said two side portions, said U-shaped excitation-detection transducer configured to be supported on and slidingly coupled with said curved channel with a shape of said U-shaped excitation-detection transducer conforming to a cross-sectional periphery of said curved channel, said U-shaped excitation-detection transducer selectively positioned over a portion of said curved channel over the patient's tooth at a position along the length of said dental tray, said U-shaped excitation-detection transducer comprises a pair of excitation-detection modules each disposed in a side portion of said two side portions, said each excitation-detection module comprising an excitation device and a detection device, said excitation device comprising a laser configured to excite surface acoustic waves (SAWs) in the patient's tooth and said detection device configured to receive SAWs in the patient's tooth, in response to the excitation of the SAWs of said excitation device,
   wherein a presence of a carious area of the patient's tooth is determined based on a departure of a phase velocity of received SAWs of the patient's tooth from a theoretical phase velocity of the received SAWs of the patient's tooth.

2. The system of claim 1, further comprising a third excitation-detection module disposed in said middle portion of said U-shaped excitation-detection transducer.

3. The system of claim 1, wherein said laser is configured to excite SAWs in the patient's tooth with a wavelength of about 266 nm, a pulse width of about 7 ns, a single pulse energy of about 1 mJ, and a repetition frequency of about 10 Hz.

4. The system of claim 1, wherein said dental tray is transparent to allow a detection laser beam emitted from said detection device to pass through the dental tray and reach a surface of the patient's tooth and a reflection of the detection laser beam in which SAW vibration information is embedded, to pass back through said dental tray to said detection device.

5. The system of claim 1, wherein said dental tray further comprises a platform connecting a top edge of a side wall of said two side walls interior to said curved channel, said dental tray is configured to be coupled to the patient's teeth on the patient's upper jaw, by securing the dental tray at said platform to the patient's palate.

6. The system of claim 5, wherein said platform is constructed from silicone.

7. The system of claim 1, further comprising a three-dimensional (3D) profilometer configured to measure an external contour of the patient's tooth to produce external contour measurements of the patient's tooth.

8. The system of claim 1, further comprising a camera disposed within said U-shaped excitation-detection transducer and directed at a portion of the patient's tooth.

9. A method for determining a presence and relative severity of dental caries in a patient's tooth, said method comprising:
(a) placing a dental tray on the patient's teeth encompassing the patient's tooth on one of the patient's lower jaw and upper jaw, the dental tray comprising a curved channel comprising two side walls and a middle wall;
(b) positioning an excitation-detection transducer over the patient's tooth at a position along the length of the curved channel;
(c) exciting surface acoustic waves (SAWs), in the patient's tooth, using an excitation device of the excitation-detection transducer through at least the two side walls of the curved channel;
(d) receiving SAWs in response to the excitation of the SAWs of the excitation device, in the patient's tooth, using a detector device of the excitation-detection transducer; and
(e) determining the presence and relative severity of a carious area of the patient's tooth based on a departure of a phase velocity of received SAWs of the patient's tooth from a theoretical phase velocity of the received SAWs of the patient's tooth.

10. The method of claim 9, further comprising exciting SAWs, in the patient's tooth, using the excitation device of the excitation-detection transducer through the middle wall.

11. The method of claim 9, wherein the excitation device comprises a laser configured to excite SAWs in the patient's tooth, with a wavelength of about 266 nm, a pulse width of about 7 ns, a single pulse energy of about 1 mJ, and a repetition frequency of about 10 Hz.

12. The method of claim 9, wherein the dental tray is transparent to allow a detection laser beam emitted from the detection device to pass through the dental tray and reach a surface of the patient's tooth and a reflection of the detection laser beam in which SAW vibration information is embedded, to pass back through the dental tray to the detection device.

13. The method of claim 9, wherein the dental tray further comprises a platform connecting a top edge of a side wall of the two side walls interior to the curved channel, the dental tray is configured to be coupled to the patient's teeth on the patient's upper jaw, by securing the dental tray at the platform to the patient's palate.

14. The method of claim 13, wherein the platform is constructed from silicone.

* * * * *